(12) United States Patent
Kym et al.

(10) Patent No.: US 6,436,986 B1
(45) Date of Patent: Aug. 20, 2002

(54) GLUCOCORTICOID RECEPTOR ANTAGONISTS FOR TREATMENT OF DIABETES

(75) Inventors: Philip R. Kym, Grayslake; Benjamin C. Lane, Libertyville, both of IL (US); John K. Pratt, Kenosha, WI (US); Tom von Geldern, Richmond, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/635,349

(22) Filed: Aug. 9, 2000

Related U.S. Application Data

(60) Provisional application No. 60/151,839, filed on Sep. 1, 1999.

(51) Int. Cl.$^7$ ................................. A61K 31/35
(52) U.S. Cl. ....................................... 514/454
(58) Field of Search ......................... 514/454

(56) References Cited

FOREIGN PATENT DOCUMENTS

| | | |
|---|---|---|
| GB | 2091721 | 8/1982 |
| WO | WO 99/41256 A | 8/1999 |

*Primary Examiner*—Amelia Owens
(74) *Attorney, Agent, or Firm*—Daniel W. Collins

(57) ABSTRACT

The instant invention relates to compounds of formula I

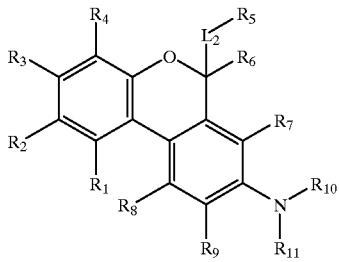

which are useful as antagonists of the glucocorticoid receptor and for treating diabetes in a mammal. In addition, any glucocorticoid receptor antagonist(s) is useful for the treatment of diabetes.

9 Claims, No Drawings

GLUCOCORTICOID RECEPTOR ANTAGONISTS FOR TREATMENT OF DIABETES

This application is related to provisional application Ser. No. 60/151,839, filed Sep. 1, 1999, from which priority is claimed pursuant to 35 U.S.C. 199(e)(1) and which is incorporated herein by reference in its entirety.

TECHNICAL FIELD

The present invention relates to glucocorticoid receptor-selective antagonists that are useful for treating diabetes.

BACKGROUND OF THE INVENTION

Type II diabetes (also referred to as non insulin-dependent Diabetes Mellitus) is a debilitating disease characterized by an abnormal elevation of blood glucose levels driven by three factors: increased hepatic glucose production, inadequate clearance of glucose via insulin mediated pathways, and decreased uptake of circulating glucose by tissues. (DeFronzo, *Diabetes Review* 5(3), 177–269, (1997)). Administration of agents that decrease hepatic glucose production are a fundamental approach to controlling blood glucose. (De Feo et al., *Am. J. Physiol.* 257, E35-E42 (1989); Rooney, et al., *J. Clin. Endocrinol. Metab.* 77, 1180–1183 (1994); Dinneen et al., *J. Clin. Invest.*, 92, 2283–2290 (1993)). Glucocorticoids have been shown to have major influences on glucose production. Glucocorticoid excess aggravates established diabetes while glucocorticoid deficiency reduces blood glucose and improves glucose control in diabetic mice. (Boyle, *Diabetes Review*, 1(3), 301–308, (1993); Naeser, *Diabetologia*, 9, 376–379 (1973); Solomon et al., *Horm, Metab. Res.*, 9, 152–156 (1977)).

The underlying mechanism responsible for these effects is the glucocorticoid-induced upregulation of key hepatic enzymes required for gluconeogenesis. (Exton et al., *Recent Prog. Horm. Res.*, 26, 411–457 (1970); Kraus-Friedmann, *Physiol. Rev.*, 64, 170–259 (1984).

Pharmaceutical agents that function as glucocorticoid receptor (GR) antagonists represent a novel approach to controlling type II diabetes.

The glucocorticoids are lipid soluble hormones synthesized in the adrenal cortex. (Neville and O'Hare, *The Adrenal Gland*. James, Ed. New York, Raven, 1–65, (1979). These molecules readily pass through cell membranes and enter the cytoplasm of target tissues, where they bind to glucocorticoid receptors sequestered in the cytoplasm by complexation with heat shock proteins. Upon binding of the hormone to its receptor, the receptor undergoes a conformational change which results in dissociation of heat shock proteins, and translocation of the ligand bound glucocorticoid receptor into the nucleus where it can either initiate or repress specific gene transcription. Transcriptional activation occurs when the ligand bound receptor complex homodimerizes, and the homodimeric receptor ligand complex binds to chromosomal DNA at sequence specific sites in the promoter region of regulated genes. (Beato, *Cell*, 56, 335–344 (1989); Yamamato, *Annu. Rev. Genet.*, 19, 209–215 (1989)). Among the genes that glucocorticoids up-regulate are several genes that play key roles in gluconeogenesis and glycogenolysis, particularly PEPCK and glucose-6-phosphatase. (Hanson and Patel, *Adv. Enzymol.*, Meister, Ed. New York, John Wiley and Sons, Inc., 203–281 (1994); Argaud et al., *Diabetes* 45, 1563–1571 (1996)).

PEPCK catalyzes the conversion of oxaloacetate to phosphoenolpyruvate and glucose-6-phosphatase catalyzes the conversion of glucose-6-phosphate into glucose, both of these transformations are required for the synthesis of glucose from oxaloacetate in the liver. Recently, it has been shown that mifepristone (RU486), a potent GR antagonist reduces mRNA levels of PEPCK and glucose-6-phosphate in the liver, and causes a 50% reduction of plasma glucose levels in obese diabetic db/db transgenic mice. (Friedman et al., *J. Biol. Chem.* 272(50), 31475–31481 (1997)). While steroid-based GR antagonists have been useful in demonstrating efficacy for in vivo glucose lowering effects, the utility of such agents is limited due to side effects resulting from potent cross-reactivity with other steroid receptors, in particular progesterone receptor (PR) and mineralocorticoid receptor (MR).

U.S. Pat. No. 5,929,058 discloses a method for treating type II diabetes by administering a combination of steroidal-agents that exhibit mineralcorticoid receptor agonist activity and glucocorticoid receptor antagonist activity. BE 890773 discloses a group of dibenzo(b,d)pyran derivatives useful for gastrointestinal ulcers, autoimmune diseases, and viral and bacterial infections. BE 823873 discloses a group of dibenzo (b,d)pyran derivatives used as anxiolytic, antidepressive, and antipsychotic agents.

Thus, it would be an important contribution to the art to provide compounds which are glucocorticoid selective non-steroidal agents that antagonize functional activity mediated by the glucocorticoid receptor, and which are useful for treating mammals suffering from type II diabetes, and for treating symptoms of type II diabetes, including hyperglycemia, inadequate glucose clearance, obesity, hyperinsulinemia, hypertriglyceridemia, high circulating glucocorticoid levels, and the like.

SUMMARY OF THE INVENTION

The present invention relates to compounds of formula I

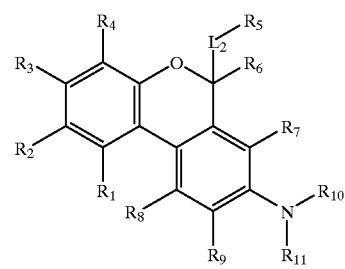

I or a pharmaceutically acceptable salt or prodrug thereof, wherein:
$R_1$ is $L_1$—$R_A$,
$R_2$, $R_3$, $R_4$, $R_7$, $R_8$, and $R_9$ are independently selected a from —$L_1$—$R_A$ or H,
$L_1$ is selected from:
 (1) a covalent bond,
 (2) —O—,
 (3) —S(O)$_t$—, where t is 0, 1, or 2,
 (4) —C(X)—, where X is O or S,
 (5) —NR$_{12}$—, where $R_{12}$ is selected from
  (a) hydrogen,
  (b) aryl,
  (c) $C_1$–$C_{12}$ cycloalkyl,
  (d) $C_1$–$C_{12}$ alkanoyl,
  (e) $C_1$–$C_{12}$ alkoxycarbonyl,
  (f) $C_1$–$C_{12}$ alkoxycarbonyl substituted with 1 to 2 aryl groups, (g) $C_1$–$C_{12}$ alkyl,
(h) $C_1$–$C_{12}$ alkyl substituted with 1 or 2 substituents independently selected from aryl or $C_3$–$C_{12}$ cycloalkyl,
(i) $C_1$–$C_{12}$ alkenyl, provided that a carbon of a carbon-carbon double bond is not attached directly to nitrogen,
(j) $C_3$–$C_{12}$ alkynyl, provided that a carbon of a carbon-carbon triple bond is not attached directly to nitrogen,
(6) —$NR_{13}C(X)NR_{14}$— where X is O or S and $R_{13}$ and $R_{14}$ are independently selected from
  (a) hydrogen,
  (b) aryl,
  (c) $C_3$–$C_{12}$ cycloalkyl,
  (d) $C_1$–$C_{12}$ alkyl,
  (e) $C_1$–$C_{12}$ alkyl substituted with 1 or 2 substituents independently selected from aryl or $C_3$–$C_{12}$ cycloalkyl,
  (f) $C_3$–$C_{12}$ alkenyl, provided that a carbon of a carbon-carbon double bond is not attached directly to nitrogen,
  (g) $C_3$–$C_{12}$ alkynyl, provided that a carbon of a carbon-carbon triple bond is not attached directly to nitrogen,
(7) —X'C(X)—, wherein X is as previously defined and X' is O or S,
(8) —C(X)X'—, wherein X and X' are as previously defined,
(9) —X'C(X)X"—, wherein X and X' are as previously defined, and X" is O or S, provided that when X is O, at least one of X' or X" is O,
(10) —$NR_{13}C(X)$—,
(11) —$C(X)NR_{13}$—,
(12) —$NR_{13}C(X)X'$—,
(13) —$X'C(X)NR_{13}$—,
(14) —$SO_2NR_{13}$—,
(15) —$NR_{13}SO_2$—, and
(16) —$NR_{13}SO_2NR_{14}$—, wherein (6)–(16) are drawn with their right ends attached to $R_A$;
$R_A$ is selected from
(1) —OH,
(2) —OG where G is a —OH protecting group,
(3) —SH,
(4) —CN,
(5) halo,
(6) haloalkoxy of one to twelve carbons,
(7) perfluoroalkoxy of one to twelve carbons,
(8) —CHO,
(9) —$NR_{12}R_{12'}$ where $R_7$ is defined previously and $R_{12'}$ is selected from
  (a) hydrogen,
  (b) aryl,
  (c) $C_3$–$C_{12}$ cycloalkyl,
  (d) $C_1$–$C_{12}$ alkanoyl,
  (e) $C_1$–$C_{12}$ alkoxycarbonyl,
  (f) $C_1$–$C_{12}$ alkoxycarbonyl substituted with 1 or 2 aryl groups,
  (g) $C_1$–$C_{12}$ alkyl,
  (h) $C_1$–$C_{12}$ alkyl substituted with 1 or 2 substituents independently selected from aryl or $C_3$–$C_{12}$ cycloalkyl,
  (i) $C_3$–$C_{12}$ alkenyl, provided that a carbon of a carbon-carbon double bond is not attached directly to nitrogen,
  (j) $C_3$–$C_{12}$ alkynyl, provided that a carbon of a carbon-carbon triple bond is not attached directly to nitrogen,
(10) —$C(X)NR_{13}R_{14}$,
(11) —$OSO_2R_{15}$ where $R_{15}$ is selected from
  (a) aryl,
  (b) $C_3$–$C_{12}$ cycloalkyl,
  (c) $C_1$–$C_{12}$ alkyl,
  (d) $C_1$–$C_{12}$ alkyl substituted with 1, 2, 3, or 4 halo substituents, and
  (e) $C_1$–$C_{12}$ perfluoroalkyl, provided that when $R_A$ is (1) to (11), $L_1$ is a covalent bond,
(12) $C_1$–$C_{12}$ alkyl,
(13) $C_2$–$C_{12}$ alkenyl, provided that a carbon of a carbon-carbon double bond is not attached directly to $L_1$ when $L_1$ is other than a covalent bond,
(14) $C_2$–$C_{12}$ alkynyl, provided that a carbon of a carbon-carbon triple bond is not attached directly to $L_1$ when $L_1$ is other than a covalent bond, where (12), (13), and (14) can be optionally substituted with 1, 2, or 3 substituents independently selected from
  (a) $C_1$–$C_{12}$ alkoxy,
  (b) —OH, provided that no two —OH groups are attached to the same carbon,
  (c) —SH, provided that no two —SH groups are attached to the same carbon,
  (d) —CN,
  (e) halo,
  (f) —CHO,
  (g) —$NO_2$,
  (h) $C_1$–$C_{12}$ haloalkoxy,
  (i) $C_1$–$C_{12}$ perfluoroalkoxy,
  (j) —$NR_{12}R_{12'}$,
  (k) =$NNR_{12}R_{12'}$,
  (l) —$NR_{12}NR_{12'}R_{12"}$ where $R_{12}$ and $R_{12'}$ are as previously defined and $R_{12"}$ is selected from
    (i) hydrogen,
    (ii) aryl,
    (iii) $C_3$–$C_{12}$ cycloalkyl,
    (iv) $C_1$–$C_{12}$ alkanoyl,
    (v) $C_1$–$C_{12}$ alkoxycarbonyl,
    (vi) $C_1$–$C_{12}$ alkoxycarbonyl substituted with 1 or 2 aryl groups,
    (vii) $C_1$–$C_{12}$ alkyl,
    (viii) $C_1$–$C_{12}$ alkyl substituted with 1 or 2 substituents independently selected from aryl or $C_3$–$C_{12}$ cycloalkyl,
    (ix) $C_3$–$C_{12}$ alkenyl, provided that a carbon-carbon double bond is not attached directly to nitrogen, and
    (x) $C_3$–$C_{12}$ alkynyl, provided that a carbon-carbon triple bond is not attached directly to nitrogen,
  (m) —$CO_2R_{16}$ where $R_{16}$ is selected from
    (i) aryl,
    (ii) aryl substituted with 1, 2, or 3 $C_1$–$C_{12}$ alkyl,
    (ii) $C_3$–$C_{12}$ cycloalkyl,
    (iii) $C_1$–$C_{12}$ alkyl, and
    (iv) $C_1$–$C_{12}$ alkyl substituted with aryl or $C_3$–$C_{12}$ cycloalkyl,
  (n) —$C(X)NR_{13}R_{14}$,
  (o) =N—$OR_{16}$,
  (p) =$NR_{16}$,
  (q) —$S(O)_rR_{16}$,
  (r) —$X'C(X)R_{16}$,
  (s) (=X), and
  (t) —$OSO_2R_{16}$,
(15) $C_3$–$C_{12}$ cycloalkyl,
(16) $C_4$–$C_{12}$ cycloalkenyl, provided that a carbon of a carbon-carbon double bond is not attached directly to $L_1$ when $L_1$ is other than a covalent bond,
where (15) and (16) can be optionally substituted with 1, 2, 3, or 4 substituents independently selected from
(a) $C_1$–$C_{12}$ alkyl,
(b) aryl,
(c) $C_1$–$C_{12}$ alkoxy,
(d) halo, and
(e) —OH, provided that no two —OH groups are attached to the same carbon,
(17) $C_1$–$C_{12}$ perfluoroalkyl,
(18) aryl, and
(19) heterocycle where (18) and (19) can be optionally substituted with 1, 2, 3, 4, or 5 substituents independently selected from
(a) $C_1$–$C_{12}$ alkyl,
(b) $C_1$–$C_{12}$ alkanoyloxy,
(c) $C_1$–$C_{12}$ alkoxycarbonyl,
(d) $C_1$–$C_{12}$ alkoxy,
(e) halo,
(f) —OH, provided that no two —OH groups are attached to the same carbon,
(g) $C_1$–$C_{12}$ thioalkoxy,
(h) $C_1$–$C_{12}$ perfluoroalkyl,
(i) —$NR_{12}R_{12'}$,
(j) —$CO_2R_{16}$,
(k) —$OSO_2R_{16}$, and
(l) (=X); or
$R_1$ and $R_2$ together are —X*—Y*—Z*— where X* is —O— or —$CH_2$—, Y* is —C(O)— or —(C($R_{17}$)($R_{18}$))$_v$— where $R_{17}$ and $R_{18}$ are independently hydrogen or $C_1$–$C_{12}$ alkyl and v is 1, 2, or 3, and Z* is selected from —$CH_2$—, —$CH_2S(O)_t$—, —$CH_2O$—, —$CH_2NR_{12}$—, —$NR_{12}$—, and —O—;
$L_2$ is selected from
(1) a covalent bond,
(2) $C_1$–$C_{12}$ alkylene,
(3) $C_1$–$C_{12}$ alkylene substituted with 1 or 2 substituents independently selected from
(a) $C_3$–$C_8$ spiroalkyl,
(b) $C_5$–$C_8$ spiroalkenyl,
(c) oxo,
(d) halo, and
(e) —OH, provided that no two —OH groups are attached to the same carbon,
(4) $C_1$–$C_{12}$ alkynylene,
(5) —$NR_{12}$—,
(6) —C(X)—,
(7) —O—, and
(8) —$S(O)_t$—; and
$R_5$ is selected from
(1) halo,
(2) —C(=$NR_{12}$)$OR_{15}$,
(3) —CN, provided that when $R_5$ is (1), (2), or (3), $L_2$ is a covalent bond,
(4) $C_1$–$C_{12}$ alkyl,
(5) $C_2$–$C_{12}$ alkynyl, provided that a carbon of a carbon-carbon triple bond is not attached directly to $L_3$ when $L_3$ is other than a covalent bond,
(6) $C_3$–$C_{12}$ cycloalkyl,
(7) heterocycle,
(8) aryl where (4)–(8) can be optionally substituted with 1, 2, 3, 4, or 5 substituents independently selected from
(a) —OH, provided that no two —OH groups are attached to the same carbon,
(b) —SH, provided that no two —SH groups are attached to the same carbon,
(c) —CN,
(d) halo,
(e) —CHO,
(f) —$NO_2$,
(g) $C_1$–$C_{12}$ haloalkoxy,
(h) $C_1$–$C_{12}$ perfluoroalkoxy,
(i) —$NR_{13'}R_{14'}$ where $R_{13'}$ and $R_{14'}$ are selected from
(i) hydrogen,
(ii) $C_1$–$C_{12}$ alkanoyl,
(iii) $C_1$–$C_{12}$ alkoxycarbonyl,
(iv) $C_1$–$C_{12}$ alkoxycarbonyl substituted with 1 to 2 phenyl substituents,
(v) $C_3$–$C_{12}$ cycloalkyl,
(vi) $C_1$–$C_{12}$ alkyl,
(vii) $C_1$–$C_{12}$ alkyl substituted with 1, 2, or 3 substituents independently selected from $C_1$–$C_{12}$ alkoxy, $C_3$–$C_{12}$ cycloalkyl, and aryl,
(viii) $C_3$–$C_{12}$ alkenyl, provided that a carbon of a carbon-carbon double bond is not directly attached to nitrogen,
(ix) $C_3$–$C_{12}$ alkynyl, provided that a carbon of a carbon-carbon triple bond is not directly attached to nitrogen,
(x) aryl,
(xi) aryl substituted with 1, 2, 3, 4, or 5 substituents independently selected from $C_1$–$C_{12}$ alkyl, $C_1$–$C_{10}$ alkanoyloxy, $C_1$–$C_{12}$ alkoxycarbonyl, $C_1$–$C_{12}$ alkoxy, halo, —OH, provided that no two —OH groups are attached to the same carbon, thioalkoxy of one to twelve carbons, perfluoroalkyl of one to twelve carbons, —$NR_{12}R_{12'}$, —$CO_2R_{15}$, —$OSO_2R_{16}$, and (=X), or
$R_{13'}$ and $R_{14'}$ together with the nitrogen atom to which they are attached form a ring selected from
(i) aziridine,
(ii) azetidine,
(iii) pyrrolidine,
(iv) piperidine,
(v) pyrazine,
(vi) morpholine,
(vii) thiomorpholine, and
(viii) thiomorpholine sulfone where (i)–(viii) can be optionally substituted with 1, 2, or 3 $C_1$–$C_{12}$ alkyl,
(j) =$NNR_{13'}R_{14'}$,
(k) —$NR_{12}NR_{13'}R_{14'}$,
(l) —$CO_2R_{13}$,
(m) —$C(X)NR_{13'}R_{14'}$,
(n) =N—$OR_{13}$,
(o) =$NR_{13}$,
(p) —$S(O)_tR_{15}$,
(q) —X'C(X)$R_{13}$,
(r) (=X),
(s) —O—($CH_2$)$_q$—Z—$R_{15}$ where $R_{15}$ is as previously defined, q is 1, 2, or 3, and Z is O or —$S(O)_t$—,
(t) —$OC(X)NR_{13'}R_{14'}$,
(u) —$OSO_2R_{16}$,
(v) $C_1$–$C_{12}$ alkanoyloxy,
(w) —$L_BR_{30}$ where $L_B$ is selected from
(i) a covalent bond,
(ii) —O—,
(iii) —$S(O)_t$—, and
(iv) —C(X)— and $R_{30}$ is selected from
(i) C1–C12 alkyl,
(ii) C1–C12 alkenyl, provided that a carbon of a carbon-carbon double bond is not attached directly to $L_B$ when $L_B$ is other than a covalent bond,
(iii) $C_1$–$C_{12}$ alkynyl, provided that a carbon of a carbon-carbon triple bond is not attached directly to $L_B$ when $L_B$ is other than a covalent bond, where (i), (ii), and (iii) can be optionally substituted with $C_3$–$C_{12}$ cycloalkyl, —OH, provided that no two —OH groups are attached to the same carbon, aryl, and heterocycle,
(iv) aryl,
(v) aryl substituted with 1, 2, 3, 4, or 5 substituents independently selected from $C_1$–$C_{12}$ alkyl, halo, —$NO_2$, and —OH, provided that no two —OH groups are attached to the same carbon,
(vi) heterocycle, and
(vii) heterocycle substituted with 1, 2, 3, 4, or 5 substituents independently selected from $C_1$–$C_{12}$ alkyl, halo, —$NO_2$, and —OH, provided that no two —OH groups are attached to the same carbon,
(x) —X'C(X)X"$R_{15}$,
(y) —C(=$NR_7$)O$R_{15}$, and
(z) —$NR_7$(X)$NR_{13'}R_{14'}$,

(9)
provided that when $R_5$ is (9), $L_3$ is other than —$NR_{12}$— or —O—,
where the carbon-carbon double bond is in the Z or E configuration, and
$R_{19}$, $R_{20}$, and $R_{21}$ are independently selected from
(a) hydrogen,
(b) halo,
(c) $C_1$–$C_{12}$ alkyl, and
(d) $C_1$–$C_{12}$ alkyl substituted with
  (i) $C_1$–$C_{12}$ alkoxy,
  (ii) —OH, provided that no two —OH groups are attached to the same carbon,
  (iii) —SH, provided that no two —SH groups are attached to the same carbon,
  (iv) —CN,
  (v) halo,
  (vi) —CHO,
  (vii) —$NO_2$,
  (viii) $C_1$–$C_{12}$ haloalkoxy,
  (ix) $C_1$–$C_{12}$ perfluoroalkoxy,
  (x) —$NR_{13'}R_{14'}$
  (xi) =$NNR_{13'}R_{14'}$,
  (xii) —$NR_{12}NR_{13'}R_{14'}$,
  (xiii) —$CO_2R_{15}$,
  (xiv) —C(X)$NR_{13'}R_{14'}$,
  (xv) =N—$OR_{15}$,
  (xvi) =$NR_{15}$,
  (xvii) —S(O)$_rR_{15}$,
  (xviii) —X'C(X)$R_{15}$,
  (xix) (=X),
  (xx) —O—$(CH_2)_q$—Z—$R_{15}$,
  (xxi) —OC(X)$NR_{13'}R_{14'}$,
  (xxii) —$L_BR_{30}$,
  (xxiii) $C_1$–$C_{12}$ alkanoyloxy,
  (xxiv) —$OSO_2R_{16}$, and
  (xxv) —$NR_7$(X)$NR_{13'}R_{14'}$, or
$R_{20}$ and $R_{21}$ together are selected from
(a) $C_3$–$C_{12}$ cycloalkyl,
(b) $C_4$–$C_{12}$ cycloalkenyl, and (allene) where $R_{22}$ and $R_{23}$ are independently hydrogen or $C_1$–$C_{12}$ alkyl, and
(10) $C_4$–$C_{12}$ cycloalkenyl carbons where the cycloalkenyl group or the ring formed by $R_{20}$ and $R_{21}$ together can be optionally substituted with one or two substituents independently selected from
(a) $C_1$–$C_{12}$ alkoxy,
(b) —OH, provided that no two —OH groups are attached to the same carbon,
(c) —SH, provided that no two —SH groups are attached to the same carbon,
(d) —CN,
(e) halo,
(f) —CHO,
(g) —$NO_2$,
(h) C1–C12 haloalkoxy,
(i) C1–C12 perfluoroalkoxy,
(j) —$NR_{13'}R_{14'}$
(k) =$NNR_{13'}R_{14'}$,
(l) —$NR_{12}NR_{13'}R_{14'}$,
(m) —$CO_2R_{15}$,
(n) —C(X)$NR_{13'}R_{14'}$,
(o) =N—$OR_{15}$,
(p) =$NR_{15}$,
(q) —S(O)$_rR_{15}$,
(r) —X'C(X)$R_{15}$,
(s) (=X),
(t) —O—$(CH_2)_q$—Z—$R_{15}$,
(u) —OC(X)$NR_{13'}R_{14'}$,
(v) —$L_BR_{30}$,
(w) C1–C12 alkanoyloxy,
(x) —$OSO_2R_{16}$, and
(y) —$NR_7$(X)$NR_{13'}R_{14'}$;
$R_6$ is hydrogen or C1–C12 alkyl; or
—$L_2$—$R_5$ and $R_6$ together are (1)
where d is 1, 2, 3, or 4 and A is selected from
(a) —$CH_2$—,
(b) —O—,
(c) —S(O)$_p$, and (d) —$NR_{12}$—, or

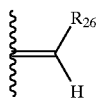

(2)
where the carbon-carbon double bond can be in the E or Z configuration and $R_{26}$ is selected from
(a) aryl,
(b) heterocycle,
(c) C1–C12 alkyl,
(d) C3–C12 cycloalkyl,
(e) C4–C12 cycloalkenyl, and
(f) C4–C12 cycloalkenyl where (a)–(f) can be optionally substituted with 1, 2, 3, 4, or 5 substituents independently selected from
  (i) C1–C12 alkoxy,
  (ii) —OH, provided that no two —OH groups are attached to the same carbon,
  (iii) —SH, provided that no two —SH groups are attached to the same carbon,
  (iv) —CN,
  (v) halo,
  (vi) —CHO,
  (vii) —$NO_2$,
  (viii) C1–C12 haloalkoxy,
  (ix) C1–C12 perfluoroalkoxy,
  (x) —$NR_{13'}R_{14'}$,
  (xi) =$NNR_{13'}R_{14'}$,
  (xii) —$NR_{12}NR_{13'}R_{14'}$,
  (xiii) —$CO_2R_{15}$,
  (xiv) —$C(X)NR_{13'}R_{14'}$,
  (xv) =N—$OR_{15}$,
  (xvi) =$NR_{15}$,
  (xvii) —$S(O)_rR_{15}$,
  (xviii) —X'$C(X)R_{15}$,
  (xix) (=X),
  (xx) —O—$(CH_2)_q$—Z—$R_{15'}$,
  (xxi) —$L_BR_{30}$,
  (xxii) C1–C12 alkanoyloxy,
  (xxiii) —$OSO_2R_{16}$, and
  (xxiv) —$NR_{12}(X)NR_{13'}R_{14'}$;
$R_{10}$ and $R_{11}$ are independently selected from
  (i) hydrogen,
  (ii) $C_1$–$C_{12}$ alkanoyl;
  (iii) $C_1$–$C_{12}$ alkoxycarbonyl;
  (iv) $C_1$–$C_{12}$ alkoxycarbonyl and is substituted with 1 or 2 phenyl substituents,
  (v) $C_1$–$C_{12}$ cycloalkyl,
  (vi) $C_1$–$C_{12}$ alkyl,
  (vii) C1–C12 alkyl substituted with 1, 2, or 3 substituents independently selected from C1–C12 alkoxy, C3–C12 cycloalkyl, and aryl,
  (viii) C3–C12 alkenyl, provided that a carbon of a carbon-carbon double bond is not directly attached to nitrogen,
  (ix) C3–C12 alkynyl, provided that a carbon of a carbon-carbon triple bond is not directly attached to nitrogen,
  (x) aryl,
  (xi) aryl substituted with 1, 2, 3, 4, or 5 substituents independently selected from C1–C12 alkyl, C1–C12 alkanoyloxy, C1–C12 alkoxycarbonyl, C1–C12 alkoxy, halo, —OH, provided that no two —OH groups are attached to the same carbon, C1–C12 thioalkoxy, C1–C12 perfluoroalkyl, —$NR_{12}R_{12'}$, —$CO_2R_{15}$, —$OSO_2R_{16}$, and (=X),
  (xii) —$S(O)_tR_{35}$, where t is 0, 1, or 2, and $R_{35}$ is selected from
    (1) $C_1$–$C_{12}$ alkyl,
    (2) $C_2$–$C_{12}$ alkenyl,
    (3) $C_2$–$C_{12}$ alkynyl where (1)–(3) can be optionally substituted,
    (4) —OH, and
    (5) —$NR_{12}R_{12'}$;
  $R_{10}$ and $R_{11}$ together with the nitrogen atom to which they are attached form a ring selected from
    (i) aziridine,
    (ii) azetidine,
    (iii) pyrrolidine,
    (iv) piperidine,
    (v) pyrazine,
    (vi) morpholine,
    (vii) thiomorpholine, and
    (viii) thiomorpholine sulfone where (i)–(viii) can be optionally substituted with 1, 2, or 3 C1–C12 alkyl, or
  $R_{10}$ and $R_7$ together with the ring that they are attached form a 5-, 6-, or 7-membered ring with 0, 1, or 2 double bonds and 0–4 substituents selected from a group consisting of alkyl, halogen, or oxo; and
  $R_{35}$ and $R_7$ together with the ring that they are attached form a 5-, 6-, or 7-membered ring with 0, 1, or 2 double bonds and 0–4 substituents selected from a group consisting of C1–C12 alkyl, halogen, or oxo.

The present invention further relates to methods of selectively antagonizing or partially antagonizing the glucocorticoid receptor.

The present invention still further relates to methods of treating mammals with type II diabetes, and/or treating or one or more of the following symptoms of type II diabetes: hyperglycemia; hyperinsulinemia; inadequate glucose clearance; obesity; hypertension, or high glucocorticoid levels, by administering one or more compounds which antagonize the glucocorticoid receptor, preferably in the absence of compounds which agonize said receptor.

The present invention still further relates to methods of treating mammals with type II diabetes, and/or treating or one or more of the following symptoms of type II diabetes: hyperglycemia; hyperinsulinemia; inadequate glucose clearance; obesity; hypertension, or high glucocorticoid levels, by administering one or more compounds of formula I.

The present invention additionally relates to pharmaceutical compositions containing compounds of formula I.

DETAILED DESCRIPTION OF THE INVENTION

The term "alkanoyl" refers to an alkyl group attached to the parent molecular group through a carbonyl group.

The term "alkanoyloxy" refers to an alkanoyl group attached to the parent molecular group through an oxygen atom.

The term "alkenyl" refers to a monovalent straight or branched chain group of two to twelve carbons derived from a hydrocarbon having at least one carbon-carbon double bond.

The term "alkoxy" refers to an alkyl group attached to the parent molecular group through an oxygen atom.

The term "alkoxycarbonyl", refers to an ester group, for example, an alkoxy group attached to the parent molecular moiety through a carbonyl group.

The term "alkyl" refers to a monovalent straight or branched chain group of one to twelve carbons derived from a saturated hydrocarbon.

The term "alkylene" refers to a divalent straight or branched chain group of one to twelve carbons derived from an alkane.

The term "alkynyl" refers to a monovalent straight or branched chain hydrocarbon of two to twelve carbons with at least one carbon-carbon triple bond.

The term "alkynylenel" refers to a divalent straight or ranched chain group of two to twelve carbons derived from an alkyne.

The term "amino refers to $-NH_2$.

The term "aryl" refers to a mono- or bicyclic carbocyclic ring system having one or two aromatic rings. The aryl group can also be fused to a cyclohexane, cyclohexene, cyclopentane or cyclopentene ring.

The term "carboxy" refers to $-CO_2H$.

The term "cycloalkenyl" refers to a monovalent group derived from a cyclic or bicyclic hydrocarbon of three to twelve carbons that has at least one carbon-carbon double bond.

The term "cycloalkyl" refers to a monovalent group three to twelve carbons derived from a saturated cyclic or bicyclic hydrocarbon.

The term "halo" refers to F, Cl, Br, or I.

The term "heterocycle" represents a represents a 4-, 5-, 6-, or 7-membered ring containing one, two, or three heteroatoms independently selected from the group consisting of nitrogen, oxygen and sulfur. The 4- and 5-membered rings have zero to two double bonds, and the 6- and 7-membered rings have zero to three double bonds. The term "heterocycle" also includes bicyclic, tricyclic and tetracyclic groups in which any of the above heterocyclic rings is fused to one or two rings independently selected from an aryl ring, a cyclohexane ring, a cyclohexene ring, a cyclopentane ring, a cyclopentene ring or another monocyclic heterocyclic ring. Heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolinyl, pyrrolyl, quinolinyl, quinoxaloyl, tetrahydrofuryl, tetrahydroisoquinolyl, tetrahydroquinolyl, tetrazolyl, thiadiazolyl, thiazolidinyl, thiazolyl, thienyl, thiomorpholinyl, triazolyl, and the like.

Heterocyclics also include bridged bicyclic groups wherein a monocyclic heterocyclic group is bridged by an alkylene group such as

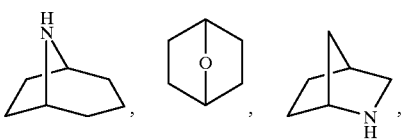

and the like.

Heterocyclics also include compounds of the formula

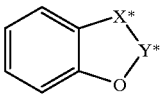

where X* is selected from $-CH_2-$, $-CH_2O-$ and $-O-$, and Y* is selected from $-C(O)-$ and $-(C(R")_2)_v-$, where R" is hydrogen or alkyl of one to four carbons, and v is 1–3. These heterocycles include 1,3-benzodioxolyl, 1,4-benzodioxanyl, and the like.

The term "heterocycloalkyl" as used herein, refers to a non-aromatic, partially unsaturated or fully saturated 4- to 8-membered ring having from one or two heteroatoms independently selected from oxygen, sulfur and nitrogen, in which the nitrogen and sulfur heteroatoms can optionally be oxidized and the nitrogen heteroatom can optionally be quaternized.

The term "N-protected amino" refers to groups intended to protect an amino group against undersirable reactions during synthetic procedures. Commonly used N-protecting groups are disclosed in Greene, "Protective Groups In Organic Synthesis," (John Wiley & Sons, New York (1981)). Preferred N-protecting groups are formyl, acetyl, benzoyl, pivaloyl, t-butylacetyl, phenylsulfonyl, benzyl, t-butyloxycarbonyl (Boc), and benzyloxycarbonyl (Cbz).

The term "O-protected carboxy" refers to a carboxylic acid protecting ester or amide group typically employed to block or protect the carboxylic acid functionality while the reactions involving other functional sites of the compound are performed. Carboxy protecting groups are disclosed in Greene, "Protective Groups in Organic Synthesis" (1981). Additionally, a carboxy protecting group can be used as a prodrug whereby the carboxy protecting group can be readily cleaved in vivo , for example by enzymatic hydrolysis, to release the biologically active parent. Such carboxy protecting groups are well known to those skilled in the art, having been extensively used in the protection of carboxyl groups in the penicillin and cephalosporin fields as described in U.S. Pat. No. 3,840,556 and 3,719,667.

The term "oxo" refers to (=O).

The term "pharmaceutically acceptable prodrugs" represents those prodrugs of the compounds of the present invention which are, within the scope of sound medical judgement, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention.

The term "prodrug" represents compounds which are rapidly transformed in vivo to the parent compound of the above formula, for example, by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The term "pharmaceutically acceptable salt" represents those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. Pharmaceutical Sciences, 66:1–19 (1977). The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, alerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Compounds of the present invention can exist as stereoisomers where asymmetric or chiral centers are present. These compounds are designated by the symbols "R" or "S," depending on the configuration of substitiuents around the chiral carbon atom. The present invention contemplates various stereoisomers and mixtures thereof. Stereoisomers include enantiomers and diastereomers, and equal mixtures of enantiomers are designated (±). Individual stereoisomers of compounds of the present invention can be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of enantiomers on chiral chromatographic columns.

Geometric isomers can also exist in the compounds of the present invention. The present invention contemplates the various geometric isomers and mixtures thereof resulting from the arrangement of substituents around a carbon-carbon double bond or arrangement of substitutents around a ring. Substituents around a carbon-carbon double bond are designated as being in the Z or E configuration where the term "Z" represents substituents on the same side of the carbon-carbon double bond and the term "E" represents substituents on opposite sides of the carbon-carbon double bond. The arrangement of substituents around a ring are designated as cis or trans where the term "cis" represents substituents on the same side of the plane of the ring and the term "trans" represents substituents on opposite sides of the plane of the ring. Mixtures of compounds where the substitutients are disposed on both the same and opposite sides of plane of the ring are designated cis/trans.

Methods for Radioligand Binding Studies with Human Glucocorticoid and Progesterone Receptor Cytosol The procedure described in Anal. Biochem. 1970, 37, 244–252, hereby incorporated by reference, was used. Briefly, cytosol preparations of human glucocorticoid receptor-[GRX]isoform and human progesterone receptor-A [PRA] isoform were obtained from Ligand Pharmaceuticals (San Diego, Calif.). Both receptor cDNAs were cloned into baculovirus expression vectors and expressed in insect SF21 cells. [$^3$H]-dexamethasone (Dex, specific activity 82–86 Ci/mmole) and [$^3$H]-progesterone (Prog, specific activity 97–102 Ci/mmol) were purchased from Amersham Life Sciences (Arlington Heights, Ill.). Glass fiber type C multiscreen MAFC NOB plates were from Millipore (Burlington, Mass.). Hydroxyapatide Bio-Gel HTP gel was from Bio-Rad Laboratories (Hercules, Calif.). Tris (hydroxymethyl)aminomethane (Tris), ethylenediaminetetraacetic acid (EDTA), glycerol, dithiothreitol (DTT) and sodium moylybdate were obtained from Sigma Chemicals (St. Louis, Mo.). Microscint-20 scintillation fluid was from Packard Instrument (Meriden, Conn.).

Stock solutions (32 mM) of compounds were prepared in dimethylsulfoxide (DMSO), and 50×solutions of test compounds were prepared from the 32 mM solution with a 50:50 mixture of DMSO/ethanol. The 50×solution was then diluted with binding buffer that contained 10 mM Tri-HCl, 1.5 mM EDTA, 10% glycerol, 1 mM DTT, 20 mM sodium molybdate, pH 7.5 @ 4° C. 1% DMSO/ethanol was present in the binding assay.

GRX and PRA binding reactions were performed in Millipore Multiscreen plates. For GR binding assays, [$^3$H]-Dex (~35,000 dpm (~0.9 nM)), GRX cytosol (~35 μg protein), test compounds and binding buffer were mixed in a total volume of 200 μL and incubated at 4° C. overnight in a plate shaker. Specific binding was defined as the difference between binding of [$^3$H]Dex in the absence and in the presence of 1 μM unlabelled Dex.

For PR binding assays, [$^3$H]Prog (~36,000 dpm (~0.8 nM)), PRA cytosol (~40 μg protein), test compounds and binding buffer were mixed in a total volume of 200 μL and incubated at 4° C. at overnight in a plate shaker. Specific binding was defined as the difference between binding of [$^3$H]Prog in the absence and in the presence of 3 μM unlabelled Prog.

After an overnight incubation, 50 μL of hydroxyapatite (25% weight/volume) slurry were added to each well and plates were incubated for 10 min at ° C. in a plate shaker. Plates were suctioned with a Millipore vacuum manifold and each well was rinsed with 300 μL of ice-cold binding buffer. A 250 μL aliquot of Packard Microscint-20 was added to each well and the wells were shaken at room temperature for 20 minutes. The amount of radioactivity was determined with a Packard TopCount plate reader.

Determination of Inhibition Constant (Ki)

The concentration of test compounds that inhibited 50% of specific binding ($IC_{50}$) was determined from a Hill analysis of the competitive binding experiments. The Ki of test compounds was determined using the Cheng-Prusoff equation $Ki=IC_{50}/(1+[L^*]/[K_L])$ where $L^*$ is the concentration of radioligand and $K_L$ is the dissociation constant of the radioligand determined from saturation analysis. For GRX, $K_L$ was ~1.5 nM, and for PRA, $K_L$ was ~4.5 nM. The inhibitory potencies of compounds of this invention and their selectivity for GR and PR receptors may be determined.

The present invention also provides pharmaceutical compositions, which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants. Conversely, reduced particle size may maintain biological activity.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Abbreviations that have been used in the descriptions of the scheme and the examples that follow are: $BF_3.OEt_2$ for boron trifluoride diethyl ether complex; DMF for N,N-dimethylformamide, DMSO for dimethylsulfoxide; and THF for tetrahydrofuran.

The compounds and processes of the present invention will be better understood in connection with the following synthetic Scheme which illustrates the methods by which the compounds of the invention can be prepared.

Scheme I

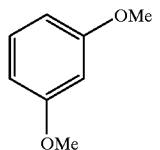

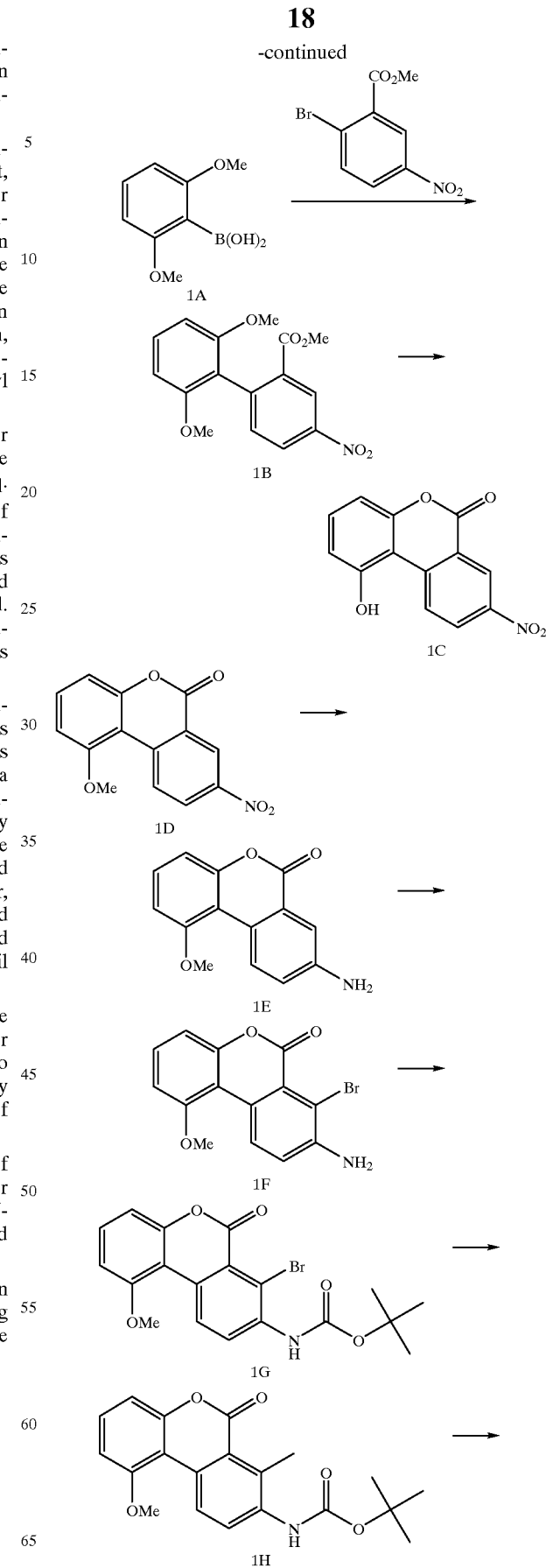

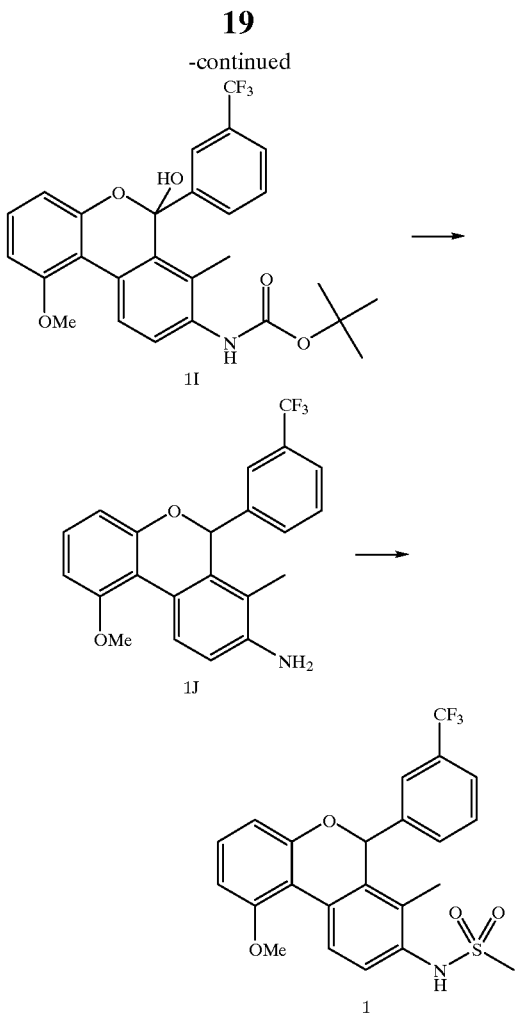

As exemplified in Scheme 1, resorcinol dimethyl ether can be metallated with a strong base such as n- or sec-butyllithium, treated with a trialkoxyborate such as trimethyl- or triisopropylborate and hydrolyzed with acid such as 2M HCl to provide boronic acid 1A. Treatment of 1A with methyl 5-nitro-2-bromobenzoate in the presence of a palladium catalyst such as tetrakis(triphenylphosphine) palladium(0) or dichlorobis(triphenylphosphine)palladium (II) provides biphenyl 1B. Demethylation of 1B may be accomplished with reagents such as BBr₃, to provide hydroxylactone 1C, which is then treated with alkylating agents such as methyl iodide to provide 1D. Conversion of 1D to amine 1E can be accomplished using hydrogen gas and a palladium catalyst such as 10% palladium on carbon. Treatment of 1E with agents such as N-bromosuccinimide or pyridinium tribromide results in regioselective bromination to form 1F, which is protected as its t-butyl carbamate 1G by treatment with triphosgene and t-butyl alcohol. Conversion of 1G to 1H may be accomplished using palladium catalysts such as [1,1-bis(diphenylphosphino)ferrocene-]dichloropalladium(II) or tetrakis(triphenylphosphine) palladium(0) in the presence of ligands such as tetramethyltin or isopropenyltrimethyltin. Introduction of functionalization at the C-5 position may be achieved through addition of organometallic reagents such as 3-trifluoromethylphenylmagnesium bromide to the C-5 carbonyl of 1H to provide 1I, followed by deoxygenation with Lewis acids such as BF₃.OEt₃ and reducing agents such as triethylsilane to provide the free aniline 1J. Final conversion of 1J to 1 may be accomplished by treatment of aniline 1J with methylsulfonyl chloride to provide sulfonamide 1.

Compounds of this invention include:
N-[1-methoxy-7-methyl-6-[3-(trifluoromethyl)phenyl]-6H-dibenzo[b,d]pyran-6-yl]methanesulfonamide;
N-(7-bromo-1-methoxy-6-phenyl-6H-dibenzo[b,d]pyran-6-yl)methanesulfonamide;
N-[7-bromo-1-methoxy-6-[3-(trifluoromethyl)phenyl]-6H-dibenzo[b,d]pyran-6-yl]methanesulfonamide;
N-[1-methoxy-7-(1-methylethenyl)-6-[3-(trifluoromethyl)phenyl]-6H-dibenzo[b,d]pyran-6-yl]methanesulfonamide; and
N-[7-ethenyl-1-methoxy-6-[3-(trifluoromethyl)phenyl]-6H-dibenzo[b,d]pyran-6-yl]methanesulfonamide.

EXAMPLES

Example 1A

A solution of 1,3-dimethoxybenzene (33.2 g, 240 mmol) in hexanes (20 mL) at −20° C. was treated sequentially with n-butyllithium (100 mL of a 2.4 M solution in hexanes, 240 mmol) and N,N,N',N'-tetramethylethylenediamine (1.81 mL, 12 mmol), stirred at 23° C. for 1.5 hours, cooled to −78° C., treated with triisopropylborate (60.9 mL, 264 mmol) in diethyl ether (60 mL) over 1.5 hours with additional diethyl ether (150 mL) added to maintain stirring, stirred at 23° C. for 2 hours, poured into ice (150 mL) and 3M HCl (150 mL), and extracted with ethyl acetate. The extract was dried (Na₂SO₄), filtered, and concentrated, during which a white solid precipitated from solution. The solid was collected by filtration and washed with hexanes to provide the desired compound.

MS (DCI/NH₃) m/z 200 (M+NH₄)⁺.

Example 1B

A mixture of Example 1A, methyl 5-nitro-2-bromobenzoate (25.8 g, 99.2 mmol), (21.7 g, 119 mmol), cesium carbonate (97.1 g, 298 mmol), and dichlorobis-(triphenylphosphine)palladium(II) (3.5 g, 5.0 mmol) in DMF (300 mL) was stirred for 24 hours at 80° C., cooled to 23° C., treated with water (600 mL), and extracted with ethyl acetate (800 mL). The extract was dried (Na₂SO₄) and concentrated, during which a light yellow solid precipitated from solution. The mixture was placed in a freezer (−20° C.) for 2 hours then filtered to provide the desired compound.

MS (DCI/NH₃) m/z 318 (M+H)⁺ and 335 (M+NH₄)⁺.

Example 1C

A solution of Example 1B (11.1 g, 35.1 mmol) in dichloromethane (60 mL) at −78° C. was treated with boron tribromide (25.0 g, 99.8 mmol),warmed to 23° C. for 1 hour, recooled to —78° C., and treated with methanol (100 mL). The mixture was warmed to 0° C., and the precipitate was collected by filtration and recrystallized from methanol to provide the desired compound.

MS (DCI/NH₃) m/z 275 (M+NH₄)⁺.

Example 1D

A mixture of Example 1C (10.7 g, 41.6 mmol) and Cs₂CO₃ (20.0 g, 61.4 mmol) in DMF (130 mL) at 23° C. was treated dropwise with methyl iodide (22.8 g, 161 mmol), stirred for 4 hours, treated with water, and extracted with 1:1 ethyl acetate/hexane. The extract was concentrated, and the resulting solid was filtered, washed with water (100 mL), and dried under vacuum to provide the desired compound.

MS (DCI/NH₃) m/z 289 (M+NH₄)⁺.

Example 1E

A suspension of Example 1D (11.2 g, 41.3 mmol) in dioxane (400 mL) at 23° C. was treated with 10% palladium on carbon (580 mg), heated at 65° C., treated with hydrogen, stirred under atmospheric pressure for 60 hours, filtered through powdered sea shells (Celite®) while hot, and concentrated during which a precipitate formed. The product was filtered and dried under vacuum to provide the desired compound. Concentration of the mother liquor to half of its original volume afforded a second crop of desired compound.

MS (DCI/NH$_3$) m/z 242 (M+H)$^+$ and 259 (M+NH$_4$)$^+$.

Example 1F

A solution of Example 1E (3.0 g, 12.5 mmol) in dioxane (300 mL) and THF (100 mL) at 23° C. was treated with pyridinium tribromide (4.0 g, 12.5 mmol) portion-wise over 15 min, stirred at 23° C. for 14 h, treated with water (400 mL), and extracted with ethyl acetate (400 mL). The extract was dried (Na2SO4), treated with charcoal (2 g), filtered through powdered sea shells (Celite®) and concentrated to provide the desired compound.

MS (DCI/NH$_3$) m/z 338 (M+NH$_4$)$^+$.

Example 1G

A suspension of Example 1F (1.8 g, 5.7 mmol) and triphosgene (0.74 g, 2.5 mmol) in THF (300 mL) was heated at reflux for 3 h. The crude reaction mixture was concentrated to dryness, and volatile byproducts were removed on a high vacuum pump for 1 h. The residue was dissolved in THF (40 mL) and t-butyl alcohol (250 mL), treated with triethylamine (0.58 g, 5.7 mmol), heated at 50° C. for 2 h, and concentrated. Flash chromatography of the residue on silica gel with 20% ethyl acetate/hexane provided the desired compound.

MS (DCI/NH$_3$) m/z 437 (M+NH$_4$)$^+$.

Example 1H

A solution of Example 1G (1.0 g, 2.4 mmol) and (1,3-bis(diphenylphosphino)ferrocene)palladium (II) chloride-dichloromethane (220 mg, 0.27 mmol) in 1-methyl-2-pyrrolidinone (2 mL) was treated with isopropenyltrimethylstannane (0.98 g, 4.8 mmol), heated at 80° C. for 24 hours, cooled to room temperature, treated with saturated KF, and extracted with ethyl acetate. The extract was washed with brine, dried (MgSO$_4$), filtered, and concentrated. The residue was purified by flash chromatography on silica gel with 5–15% ethyl acetate/hexanes to provide the desired compound.

MS (DCI/NH$_3$) m/z 373 (M+NH$_4$)$^+$.

Example 1I

A solution of Example 1H (0.29 g, 0.81 mmol) in THF (50 mL) at −30° C. was treated with a solution of 3-trifluoromethylphenylmagnesium bromide in diethyl ether (0.4 M, 12 mL, 4.9 mmol), warmed to 0° C., stirred for 20 hours, treated with saturated NH$_4$Cl, warmed to 25° C., and extracted with ethyl acetate. The extract was dried (Na$_2$SO$_4$), filtered, and concentrated. The residue was purified by flash chromatography on silica gel with 20% ethyl acetate/hexanes to provide the desired compound.

Example 1J

A solution of Example 1I (0.1 g, 0.20 mmol) in dichloromethane (30 mL) at 0° C. was treated with triethylsilane (0.23 g, 2.0 mmol) and BF$_3$.OEt$_2$ (0.28 g, 2.0 mmol), warmed to room temperature, stirred for 16 hours, and treated with saturated NaHCO$_3$. The organic layer was dried (Na$_2$SO$_4$), filtered, and concentrated. The residue was purified by flash chromatography on silica gel with 20% ethyl acetate/hexanes to provide the desired compound.

MS (DCI/NH$_3$) m/z 386 (M+H)$^+$;

Example 1

A solution of 1J (0.025 g, 0.065 mmol) in dichloromethane (7 mL) at 0° C. was treated with methanesulfonyl chloride (0.006 mL, 0.075 mmol), warmed to room temperature, stirred for 14 hours, and treated with saturated NaHCO$_3$. The organic layer was dried (Na$_2$SO$_4$), filtered, and concentrated. The residue was purified by flash chromatography on silica gel with 42% ethyl acetate/hexanes to provide the desired compound.

mp=217–218° C. MS (DCI/NH$_3$) m/z 481 (M+NH$_4$)$^+$, 464 (M+H)$^+$; $^1$H NMR (300 MHz, DMSO-d$_6$) 9.25 (s, 1H), 8.3 (d, 1H), 7.61 (d, 1H), 7.55 (s, 1H), 7.50 (t, 1H), 7.41 (d, 1H), 7.28 (d, 1H), 7.12 (t, 1H), 6.7 (s, 1H), 6.69 (dd, 1H), 6.6 (dd, 1H), 3.85 (s, 3H), 3.02 (s, 3H), 2.2 (s, 3H);

We claim:

1. A compound of formula I

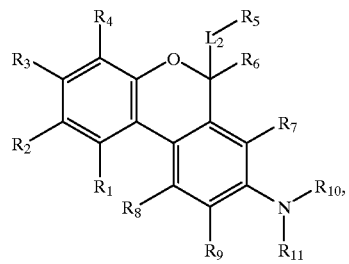

or a pharmaceutically acceptable salt or prodrug thereof, wherein:

R$_1$ is L$_1$—R$_A$,

R$_2$, R$_3$, R$_4$, R$_7$, R$_8$, and R$_9$ are independently selected from H, OH, OG where G is an OH protecting group, alkoxy of 1–4 carbons, haloalkoxy of 1 to 4 carbons, halogen or C$_1$–C$_{12}$ alkyl, L$_1$ is selected from:
 (1) a covalent bond,
 (2) —O—,
 (3) —S(O)$_t$—, where t is 0, 1, or 2,
 (4) —C(X)—, where X is O or S,
 (5) —NR$_{12}$—, where R$_{12}$ is selected from
  (a) hydrogen,
  (b) C$_1$–C$_6$[C$_{12}$]cycloalkyl,
  (c) C$_1$–C$_6$[C$_{12}$]alkyl,
 (7) —X'C(X)—, wherein X is as previously defined and X' is O or S,
 (8) —C(X)X'—, wherein X and X' are as previously defined,
 (9) —X'C(X)X"—, wherein X and X' are as previously defined, and X" is O or S, provided that when X is O, at least one of X' or X" is O,
 (10) —NR$_{13}$C(X)—,
 (11) —C(X)NR$_{13}$—,
 (12) —NR$_{13}$C(X)X'—,
 (13) —X'C(X)NR$_{13}$—,
 (14) —SO$_2$NR$_{13}$—,
 (15) —NR$_{13}$SO$_2$—, and

(16) —NR$_{13}$SO$_2$NR$_{14}$—,
wherein (6)–(16) are drawn with their right ends attached to R$_A$;
R$_A$ is selected from
- (1) —OH,
- (2) —OG where G is a —OH protecting group,
- (3) —SH,
- (4) —CN,
- (5) halo,
- (6) haloalkoxy of one to twelve carbons,
- (7) perfluoroalkoxy of one to twelve carbons,
- (8) —CHO,
- (9) —NR$_{12}$R$_{12'}$ where R$_7$ is defined previously and R$_{12'}$ is selected from
  - (a) hydrogen,
  - (b) C$_1$–C$_{12}$ alkyl substituted with 1 or 2 substituents independently selected from aryl or C$_3$–C$_{12}$ cycloalkyl,
  - (c) C$_3$–C$_{12}$ alkenyl, provided that a carbon of a carbon-carbon double bond is not attached directly to nitrogen,
  - (d) C$_3$–C$_{12}$ alkynyl, provided that a carbon of a carbon-carbon triple bond is not attached directly to nitrogen,
  - (b) C$_1$–C$_{12}$ alkyl, and
  - (c) C$_1$–C$_{12}$ perfluoroalkyl, provided that when R$_A$ is (1) to (11), L$_1$ is a covalent bond,
- (12) C$_1$–C$_{12}$ alkyl,
- (13) C$_2$–C$_{12}$ alkenyl, provided that a carbon of a carbon-carbon double bond is not attached directly to L$_1$ when L$_1$ is other than a covalent bond,
- (14) C$_2$–C$_{12}$ alkynyl, provided that a carbon of a carbon-carbon triple bond is not attached directly to L$_1$ when L$_1$ is other than a covalent bond, where (12), (13), and (14) can be optionally substituted with 1, 2, or 3 substituents independently selected from
  - (a) C$_1$–C$_{12}$ alkoxy,
  - (b) —OH, provided that no two —OH groups are attached to the same carbon,
  - (c) —SH, provided that no two —SH groups are attached to the same carbon,
  - (d) —CN,
  - (e) halo,
  - (f) —CHO,
  - (g) —NO$_2$,
  - (h) C$_1$–C$_{12}$ haloalkoxy,
  - (i) C$_1$–C$_{12}$ perluoroalkoxy,
  - (n) —C(X)NR$_{13}$R$_{14}$,
  - (o) =N—OR$_{16}$,
  - (p) =NR$_{16}$,
  - (q) —S(O)$_t$R$_{16}$,
  - (r) —X'C(X)R$_{16}$,
  - (s) (=X), and
  - (t) —OSO$_2$R$_{16}$,
- (15) C$_3$–C$_{12}$ cycloalkyl,
- (16) C$_4$–C$_{12}$ cycloalkenyl, provided that a carbon of a carbon-carbon double bond is not attached directly to L$_1$ when L$_1$ is other than a covalent bond, where (15) and (16) can be optionally substituted with 1, 2, 3, or 4 substituents independently selected from
  - (a) C$_1$–C$_{12}$ alkyl,
  - (b) aryl,
  - (c) C$_1$–C$_{12}$ alkoxy,
  - (d) halo, and
  - (e) —OH, provided that no two —OH groups are attached to the same carbon,
- (17) C$_1$–C$_{12}$ perfluoroalkyl, R$_1$ and R$_2$ together are oX*—Y*—Z*— where X* is —O— or —CH$_2$—, Y* is —C(O)— or —(C(R$_{17}$)(R$_{18}$))$_v$— where R$_{17}$ and R$_{18}$ are independently hydrogen or C$_1$–C$_{12}$ alkyl and v is 1, 2, or 3, and Z* is selected from —CH$_2$—, —CH$_2$S(O)$_t$—, —CH$_2$O—, —CH$_2$NR$_{12}$—, —NR$_{12}$—, and —O—;

L$_2$ is selected from
- (1) a covalent bond,
- (2) C$_1$–C$_{12}$ alkylene,
- (3) C$_1$–C$_{12}$ alkylene substituted with 1 or 2 substituents independently selected from
  - (a) C$_3$–C$_8$ spiroalkyl,
  - (b) C$_5$–C$_8$ spiroalkenyl,
  - (c) oxo,
  - (d) halo, and
  - (e) —OH, provided that no two —OH groups arc attached to the same carbon,
- (4) C$_1$–C$_{12}$ alkynylene,
- (5) —NR$_{12}$—,
- (6) —C(X)—,
- (7) —O—, and
- (8) —S(O)$_t$—; and R$_5$ is selected from
- (1) halo,
- (2) —CN, provided that when R$_5$ is (1), (2), or (3), L$_2$ is a covalent bond,
- (3) C$_1$–C$_{12}$ alkyl,
- (4) C$_2$–C$_{12}$ alkynyl, provided that a carbon of a carbon-carbon triple bond is not attached directly to L$_3$ when L$_3$ is other than a covalent bond,
- (5) C$_3$–C$_{12}$ cycloalkyl,
- (6) heterocycle,
- (7) aryl where (3)–(7) can be optionally substituted with 1, 2, 3, 4, or 5 substituents independently selected from
  - (a) —OH, provided that no two —OH groups are attached to the same carbon,
  - (b) —SH, provided that no two —SH groups are attached to the same carbon,
  - (c) —CN,
  - (d) halo,
  - (e) —CHO,
  - (f) —NO$_2$,
  - (g) C$_1$–C$_{12}$ haloalkoxy,
  - (h) C$_1$–C$_{12}$ perfluoroalkoxy,
  - (i) —NR$_{13'}$R$_{14'}$ where R$_{13'}$ and R$_{14'}$ are selected from
    - (i) hydrogen,
    - (ii) C$_1$–C$_{12}$ alkanoyl,
    - (iii) C$_1$–C$_{12}$ alkoxycarbonyl,
    - (iv) C$_1$–C$_{12}$ alkoxycarbonyl substituted with 1 to 2 phenyl substituents,
    - (v) C$_3$–C$_{12}$ cycloalkyl,
    - (vi) C$_1$–C$_{12}$ alkyl,
    - (vii) C$_1$–C$_{12}$ alkyl substituted with 1, 2, or 3 substituents independently selected from C$_1$–C$_{12}$ alkoxy, C$_3$–C$_{12}$ cycloalkyl, and aryl,
    - (viii) C$_3$–C$_{12}$ alkenyl, provided that a carbon of a carbon-carbon double bond is not directly attached to nitrogen,
    - (ix) C$_3$–C$_{12}$ alkynyl, provided that a carbon of a carbon-carbon triple bond is not directly attached to nitrogen,
    - (x) aryl,
    - (xi) aryl substituted with 1, 2, 3, 4, or 5 substituents independently selected from C$_1$–C$_{12}$ alkyl, C$_1$–C$_{10}$ alkanoyloxy, C$_1$–C$_{12}$ alkoxycarbonyl, $C_1$–$C_{12}$ alkoxy, halo, —OH, provided that no two —OH groups are attached to the same carbon, thioalkoxy of one to twelve carbons, perfluoroalkyl of one to twelve carbons, —$NR_{12}R_{12'}$, —$CO_2R_{15}$, —$OSO_2R_{16}$, and (=X), or $R_{13'}$ and $R_{14'}$ together with the nitrogen atom to which they are attached form a ring selected from (i) aziridine,
(ii) azetidine,
(iii) pyrrolidine,
(iv) piperidine,
(v) pyrazine,
(vi) morpholine,
(vii) thiomorpholine, and
(viii) thiomorpholine sulfone where (i)–(viii) can be optionally substituted with 1, 2, or 3 $C_1$–$C_{12}$ alkyl, (j) $CO_2R_{13}$,
(k) —$C(X)NR_{13'}R_{14'}$,
(l) =N—$OR_{13}$,
(m) —X'C(X)$R_{13}$, (n) (=X),
(o) —O—$(CH_2)_q$—Z—$R_{15}$ where $R_{15}$ is as previously defined, q is 1, 2, or 3, and Z is O or —$S(O)_t$—,
(p) —$OC(X)NR_{13'}R_{14'}$,
(q) —$OSO_2R_{16}$,
(r) $C_1$–$C_{12}$ alkanoyloxy,
(s) —$L_BR_{30}$ where $L_B$ is selected from
 (i) a covalent bond,
 (ii) —O—,
 (iii) —$S(O)_t$—, and
 (iv) —C(X)— and $R_{30}$ is selected from
 (i) $C_1$–$C_{12}$ alkyl,
 (ii) $C_1$–$C_{12}$ alkenyl, provided that a carbon of a carbon-carbon double bond is not attached directly to $L_B$ when $L_B$ is other than a covalent bond,
 (iii) $C_1$–$C_{12}$ alkynyl, provided that a carbon of a carbon-carbon triple bond is not attached directly to $L_B$ when $L_B$ is other than a covalent bond, where (i), (ii), and (iii) can be optionally substituted with $C_3$–$C_{12}$ cycloalkyl, —OH, provided that no two —OH groups are attached to the same carbon, aryl, and heterocycle,
 (iv) aryl,
 (v) aryl substituted with 1, 2, 3, 4, or 5 substituents independently selected from $C_1$–$C_{12}$ alkyl, halo, —$NO_2$, and —OH, provided that no two —OH groups are attached to the same carbon,
 (vi) heterocycle, and
 (vii) heterocycle substituted with 1, 2, 3, 4, or 5 substituents independently selected from $C_1$–$C_{12}$ alkyl, halo, —$NO_2$, and —OH, provided that no two —OH groups are attached to the same carbon, (x) —X'C(X)X"$R_{15}$,
(y) —C(=$NR_7$)$OR_{15}$, and (z) —$NR_7(X)NR_{13'}OR_{14'}$,

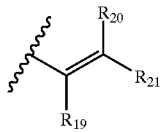

(9)
provided that when $R_5$ is (9), $L_3$ is other than —$NR_{12}$— or —O—, where the carbon-carbon double bond is in the Z or E configuration, and $R_{19}$, $R_{20}$, and $R_{21}$ are independently selected from
(a) hydrogen,
(b) halo,
(c) $C_1$–$C_{12}$ alkyl, and
(d) $C_1$–$C_{12}$ alkyl substituted with
 (i) $C_1$–$C_{12}$ alkoxy,
 (ii) —OH, provided that no two —OH groups are attached to the same carbon,
 (iii) —SH, provided that no two —SH groups are attached to the same carbon,
 (iv) —CN,
 (v) halo,
 (vi) —CHO,
 (vii) —$NO_2$,
 (viii) $C_1$–$C_{12}$ haloalkoxy,
 (ix) $C_1$–$C_{12}$ perfluoroalkoxy,
 (x) —$NR_{13'}R_{14'}$,
 (xi) =$NNR_{13'}R_{14'}$,
 (xii) —$NR_{12}NR_{13'}R_{14'}$,
 (xiii) —$CO_2R_{15}$,
 (xiv) —$C(X)NR_{13'}R_{14'}$,
 (xv) =N—$OR_{15}$,
 (xvi) =$NR_{15}$,
 (xvii) —$S(O)_tR_{15}$,
 (xviii) —X'C(X)$R_{15}$,
 (xix) (=X),
 (xx) —O—$(CH_2)_q$—Z—$R_{15}$,
 (xxi) —$OC(X)NR_{13'}R_{14'}$,
 (xxii) —$L_BR_{30}$,
 (xxiii) $C_1$–$C_{12}$ alkanoyloxy,
 (xxiv) —$OSO_2R_{16}$, and
 (xxv) —$NR_7(X)NR_{13'}R_{14'}$, or
$R_{20}$ and $R_{21}$ together are selected from
 (a) $C_3$–$C_{12}$ cycloalkyl,
 (b) $C_4$–$C_{12}$ cycloalkenyl, and
 (c)

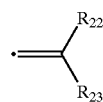

(allene) where $R_{22}$ and $R_{23}$ are independently hydrogen or $C_1$–$C_{12}$ alkyl, and
(10) $C_4$–$C_{12}$ cycloalkenyl carbons where the cycloalkenyl group or the ring formed by $R_{20}$ and $R_{21}$ together can be optionally substituted with one or two substituents independently selected from
 (a) $C_1$–$C_{12}$ alkoxy,
 (b) —OH, provided that no two —OH groups are attached to the same carbon,
 (c) —SH, provided that no two —SH groups are attached to the same carbon,
 (d) —CN, (e) halo,
(f) —CHO,
(g) —NO$_2$,
(h) C1–C12 haloalkoxy,
(i) C1–C12 perfluoroalkoxy,
(j) —NR$_{13'}$R$_{14'}$,
(k) =NNR$_{13'}$R$_{14'}$,
(l) —NR$_{12'}$NR$_{13'}$R$_{14'}$,
(m) —CO$_2$R$_{15}$,
(n) —C(X)NR$_{13'}$R$_{14'}$,
(o) =N—OR$_{15}$,
(p) =NR$_{15}$,
(q) —S(O)$_r$R$_{15}$,
(r) —X'C(X)R$_{15}$,
(s) (=X),
(t) —O—(CH$_2$)$_q$—Z—R$_{15}$,
(u) —OC(X)NR$_{13'}$R$_{14'}$,
(v) —L$_B$R$_{30}$,
(w) C1–C12 alkanoyloxy,
(x) —OSO$_2$R$_{16}$, and
(y) —NR$_7$(X)NR$_{13'}$R$_{14'}$;
R$_6$ is hydrogen or C1–C12 alkyl; or
R$_{10}$ and R$_{11}$ are independently selected from
(i) hydrogen,
(ii) C$_1$–C$_{12}$ alkanoyl;
(iii) C$_1$–C$_{12}$ alkoxycarbonyl;
(iv) C$_1$–C$_{12}$ alkoxycarbonyl and is substituted with 1 or 2 phenyl substituents,
(v) C$_1$–C$_{12}$ cycloalkyl,
(vi) C$_1$–C$_{12}$ alkyl,
(vii) C1–C12 alkyl substituted with 1, 2, or 3 substituents independently selected from C1–C12 alkoxy, C3–C12 cycloalkyl, and aryl,
(viii) C3–C$_{12}$ alkenyl, provided that a carbon of a carbon-carbon double bond is not directly attached to nitrogen,
(ix) C3–C$_{12}$ alkynyl, provided that a carbon of a carbon-carbon triple bond is not directly attached to nitrogen,
(x) aryl,
(xi) aryl substituted with 1, 2, 3, 4, or 5 substituents independently selected from C1–C12 alkyl, C1–C12 alkanoyloxy, C1–C12 alkoxycarbonyl, C1–C12 alkoxy, halo, —OH, provided that no twvo —OH groups are attached to the same carbon, C1–C12 thioalkoxy, C1–C12 perfluoroalkyl, —NR$_{12}$R$_{12'}$, —CO$_2$R$_{15}$, —OSO$_2$R$_{16}$, and (=X),
(xii) —S(O)$_t$R$_{35}$, where t is 0, 1, or 2, and R$_{35}$ is selected from
(1) C$_1$–C$_{12}$ alkyl,
(2) C$_2$–C$_{12}$ alkenyl,
(3) C$_2$–C$_{12}$ alkynyl where (1)–(3) can be optionally substituted,
(4) —OH, and
(5) —NR$_{12}$R$_{12'}$;
R$_{10}$ and R$_{11}$ together with the nitrogen atom to which they are attached form a ring selected from
(i) aziridine,
(ii) azetidine,
(iii) pyrrolidine,
(iv) piperidine,
(v) pyrazine,
(vi) morpholine,
(vii) thiomorpholine, and
(viii) thiomorpholine sulfone where (i)–(viii) can be optionally substituted with 1, 2, or 3 C2–C12 alkyl, and
R$_{35}$ and R$_7$ together with the ring that they are attached form a 5-, 6-, or 7-membered ring with 0, 1, or 2 double bonds and 0–4 substituents selected from a group consisting of C1–C12 alkyl, halogen, or oxo.

2. A compound according to claim 1 where
R$_1$ is —L$_1$—R$_A$ where
L$_1$ is selected from
(1) a covalent bond,
(2) —O—,
(3) —C(X)X'— where X and X' are O,
(4) —X'C(X)— where X and X' are O, and
(5) —X'C(X)X"— where X, X', and X" are O and
R$_A$ is selected from
(1) alkyl of one to twelve carbons,
(2) alkenyl of two to twelve carbons,
(3) alkynyl of two to twelve carbons where (1)–(3) can be optionally substituted,
(4) —OH, and
(5) —NR$_{12}$R$_{12'}$;
R$_2$ is hydrogen or —L$_1$—R$_A$ where L$_1$ is —O— and R$_A$ is alkyl of one to twelve carbons;
R$_3$, R$_4$, R$_8$, and R$_9$ are hydrogen,
L$_2$ is a covalent bond or —NR$_{12}$—;
R$_5$ is selected from
(1) halo,
(2) —C(=NR$_7$)OR$_{10}$,
(3) —CN,
(4) alkyl of one to twelve carbons,
(5) alkynyl of two to twelve carbons,
(6) heterocycle,
(7) aryl,
(8)

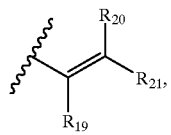

and (9) cycloalkenyl of four to twelve carbons where (4)–(7), (9), and the substituents defined by R$_{19}$, R$_{20}$, and R$_{21}$ in (8) can be optionally substituted; and
R$_6$ is hydrogen; or
—L$_2$—R$_5$ and R$_6$ together are

where the substituents defined by R$_{26}$ can be optionally substituted,
R$_7$ is hydrogen; or R$_7$ and R$_{10}$ together with the ring that they are attached form a 5-, 6-, or 7-membered ring with 1–2 double bonds an 0–4 substituents selected from
a group consisting of alkyl, halogen, or oxo, $R_{10}$ and $R_{11}$ are independantly selected from hydrogen; $C(O)R_{35}$, or $—S(O)_tR_{35}$, where t is 0, 1, or 2, and $R_{35}$ is selected from
(1) alkyl of one to twelve carbons,
(2) alkenyl of two to twelve carbons,
(3) alkynyl of two to twelve carbons where (1)–(3) can be optionally substituted,
(4) $—OR_{15}$, and
(5) $—NR_{12}R_{12'}$.

3. A compound according to claim 2 where $L_1$ is O and $R_A$ is alkyl of one to twelve carbons that can be optionally substituted.

4. A compound according to claim 3 where $R_{10}$ is selected from $S(O)_tR_{35}$, where t is 0, 1, or 2, and $R_{35}$ is selected from alkyl of one to four carbons.

5. A compound according to claim 4 selected from

N-[1-methoxy-7-methyl-6-[3-(trifluoromethyl)phenyl]-6H-dibenzo[b,d]pyran-6-yl]methanesulfonamide;

N-[7-bromo-1-methoxy-6-phenyl-6H-dibenzo[b,d]pyran-6-yl]methanesulfonamide;

N-[7-bromo-1-methoxy-6-[3-(trifluoromethyl)phenyl]-6H-dibenzo[b,d]pyran-6-yl]methanesulfonamide;

N-[1-methoxy-7-(1-methylethenyl)-6-[3-(trifluoromethyl)phenyl]-6H-dibenzo[b,d]pyran-6-yl]methanesulfonamide;

N-[7-ethenyl-1-methoxy-6-[3-(trifluoromethyl)phenyl]-6H-dibenzo[b,d]pyran-6-yl]methanesulfonamide; and N-[7-bromo-1-methoxy-6-(3,5-dimethylphenyl)-6H-dibenzo[b,d]pyran-6-yl]methanesulfonamide.

6. A method of selectively modulating the antagonism effects of the glucocorticoid receptor in a mammal comprising administering an effective amount of a compound of claim 1.

7. A method of treating diabetes in a mammal comprising administering an effective amount of a compound of claim 1.

8. A method of treating diabetes in a mammal comprising administering an effective amount of a glucocorticoid receptor antagonist.

9. A method according to claim 8, wherein said glucocorticoid receptor antagonist is administered in the absence of a glucocorticoid receptor agonist.

* * * * *

UNITED STATES PATENT AND TRADEMARK OFFICE
CERTIFICATE OF CORRECTION

PATENT NO.   : 6,436,986 B1
DATED        : August 20, 2001
INVENTOR(S)  : Philip R. Kym et al.

It is certified that error appears in the above-identified patent and that said Letters Patent is hereby corrected as shown below:

Column 24,
Lines 1 and 2, replace "$R_1$ and $R_2$ together are-o X*-Y*-Z*-were X* is-O-or-CH2-" with -- "$R_1$ and $R_2$ together are-X*-Y*-Z*-were X* is -O-or-CH2-," --.

Signed and Sealed this

Fifteenth Day of July, 2003

JAMES E. ROGAN
*Director of the United States Patent and Trademark Office*